United States Patent
Dep et al.

(10) Patent No.: US 7,605,366 B2
(45) Date of Patent: Oct. 20, 2009

(54) NUCLEAR DENSITY GAUGE

(75) Inventors: Wewage Hiran Linus Dep, Chapel Hill, NC (US); Robert Ernest Troxler, Raleigh, NC (US); Raffaello Verna, Creedmoor, NC (US)

(73) Assignee: Troxler Electronic Laboratories, Inc., Research Triangle Park, NC (US)

( * ) Notice: Subject to any disclaimer, the term of this patent is extended or adjusted under 35 U.S.C. 154(b) by 187 days.

(21) Appl. No.: 11/534,075

(22) Filed: Sep. 21, 2006

(65) Prior Publication Data

US 2008/0111065 A1    May 15, 2008

Related U.S. Application Data

(60) Provisional application No. 60/719,071, filed on Sep. 21, 2005.

(51) Int. Cl.
*G01V 5/12* (2006.01)
(52) U.S. Cl. ..................................... 250/253
(58) Field of Classification Search ................ 250/253, 250/308, 388, 390.06, 269.3, 498.1, 497.1; 378/89, 86
See application file for complete search history.

(56) References Cited

U.S. PATENT DOCUMENTS

| | | | | | |
|---|---|---|---|---|---|
| 4,542,472 | A | * | 9/1985 | Toms, II | 250/390.05 |
| 4,587,623 | A | * | 5/1986 | Regimand et al. | 702/90 |
| 4,641,030 | A | * | 2/1987 | Regimand | 850/63 |
| 4,701,868 | A | * | 10/1987 | Regimand | 702/137 |
| 4,766,319 | A | * | 8/1988 | Regimand | 250/390.05 |
| 5,923,726 | A | * | 7/1999 | Regimand | 378/207 |
| 6,050,725 | A | * | 4/2000 | Regimand | 378/207 |
| 6,310,936 | B1 | * | 10/2001 | Troxler et al. | 378/55 |
| 6,369,381 | B1 | * | 4/2002 | Troxler et al. | 250/252.1 |
| 6,567,498 | B1 | | 5/2003 | Troxler et al. | |
| 6,617,599 | B2 | * | 9/2003 | Weger et al. | 250/498.1 |
| 2001/0055363 | A1 | * | 12/2001 | Troxler et al. | 378/55 |

FOREIGN PATENT DOCUMENTS

WO    WO 00/52454 A2    9/2000
WO    WO 01/57505 A2    8/2001

* cited by examiner

*Primary Examiner*—David P Porta
*Assistant Examiner*—Djura Malevic
(74) *Attorney, Agent, or Firm*—Alston & Bird LLP

(57) ABSTRACT

A nuclear density gauge includes a base and at least one gamma radiation detector mounted at a predetermined location relative to an axis extending longitudinally of the base. The gauge further includes a gamma radiation source and a source mount that mounts the gamma radiation source for movement along a path between an active first position located at a first longitudinal distance from the detector and an active second position located at a second longitudinal distance from the detector. In this way, gamma radiation is detected emanating from the source and backscattered from the underlying material sample through a first path of travel when the source mount is at the first active position and through a second path of travel when the source mount is at the second active position. The source mount may also move the source from the active first and second positions to an inactive third position shielded by gamma radiation shielding material.

23 Claims, 7 Drawing Sheets

NUCLEAR DENSITY GAUGE

CROSS-REFERENCE TO RELATED APPLICATION

This application is related to and claims priority from U.S. Provisional Patent Application No. 60/719,071 filed Sep. 21, 2005, which is incorporated herein by reference.

BACKGROUND OF THE INVENTION

This invention relates to a portable test instrument, and more particularly to a nuclear gauge for measuring the density properties of a test material.

Portable nuclear gauges are frequently used in the construction industry for measuring the moisture content and density of soils, soil-stone aggregates, cement, and asphalt. One such gauge which has been commercially available for a number of years is the 3400 Series surface moisture-density gauge manufactured by Troxler Electronic Laboratories of Research Triangle Park, N.C., the assignee of the present invention.

These gauges utilize the principle of Compton scattering of gamma rays for determining the density characteristics of the test material. The aforementioned type of gauge typically employs gamma radiation sources having an activity level in the millicurie range. For example, the Troxler 3400 Series moisture-density gauge employs a cesium-137 gamma source containing approximately eight millicurie of cesium-137.

Many jurisdictions impose regulations and licensing requirements with respect to the handling and use of nuclear test instruments with gamma radiation sources in the millicurie range. However, nuclear density gauges which use nuclear sources of relatively low activity, e.g. in the microcurie range are subject to fewer and less stringent restrictions and regulations. Gauges of this type are described, for example in U.S. Pat. Nos. 4,766,319 and 6,567,498, assigned to Troxler Electronic Laboratories of Research Triangle Park, N.C., the assignee of the present application.

It is an object of the present invention to provide improvements in a nuclear density gauge, and more particularly to a nuclear density gauge of the type which uses a low activity gamma radiation source.

BRIEF SUMMARY OF THE INVENTION

The present invention provides a unique and advantageous arrangement for mounting the radiation source in a nuclear density gauge. The gauge comprises a base having a surface adapted to be positioned on a surface of a material sample and at least one gamma radiation detector carried by the base and mounted at a predetermined location relative to an axis extending longitudinally of the base. The gauge further includes a gamma radiation source and a source mount carried by the base. The source mount serves to mount the gamma radiation source for movement along a path between an active first position located at a first longitudinal distance from said at least one detector and an active second position located at a second longitudinal distance from said detector. In this way, the at least one gamma radiation detector is (are) positioned and arranged to detect gamma radiation emanating from the source and backscattered from the underlying material sample through a first path of travel when the source mount is at the first active position and through a second path of travel when the source mount is at the second active position. The source mount may also include means for moving the source from the active first and second positions to an inactive third position shielded by gamma radiation shielding material.

In one advantageous embodiment, the source mount moves the source on a linear path along a longitudinal axis of the base. The source mount includes a roller formed of a gamma radiation shielding material and having a cylindrical outer surface. The source is mounted in the roller so that the gamma radiation from the source emanates from one location on the cylindrical surface. Means is provided for rotating the roller on a path along a longitudinal axis between the active first position wherein the source is oriented downwardly toward said base and through at least one complete revolution of the roller to the active second position wherein the source is again oriented downwardly toward the base.

In another embodiment, the source mount moves the source on a non-linear path from the active first position to the active second position. In this embodiment, the source mount includes an arm that is pivotally mounted at one end and carries the source at its opposite end. By rotating the arm about its pivotal mounting point, the source is moved along an arcuate path between the active first position closer to the detector and the active second position further away from the detector.

While not being limited thereto, the source mounting arrangement of present invention as described above is especially advantageous and useful with gamma radiation sources of relatively low activity, e.g. less than 1000 microcurie, and more particularly 500 microcurie or less. In one specific embodiment, the nuclear density gauge comprises a base having a surface adapted to be positioned on a surface of a material sample and first and second gamma radiation scintillation detectors carried by the base and mounted in side-by-side relationship on opposite sides of an axis extending longitudinally of the base, where the detectors each include a photon-scintillating crystal and a photomultiplier tube cooperating with the photon-scintillating crystal for generating electrical signals proportional to the energy of the photons. Preferably, the crystals are of a square shape and are positioned next to one another on opposite sides of the longitudinal axis to form a rectangle with a longer dimension extending transverse to the longitudinal axis. The gauge further includes a gamma radiation source having a characteristic primary energy and a total activity of no more than 500 microcuries. A source mount is carried by the base and mounts the gamma radiation source at a location spaced along said longitudinal axis from the first and second detectors. The gauge further includes means for calculating a value for the density of the material sample based upon the gamma radiation detected by the first and second detectors. The source mount includes a roller formed of a gamma radiation shielding material and having a cylindrical outer surface, and wherein said source is mounted in the roller so that the gamma radiation from the source emanates from one location on the cylindrical surface. Means is provided for rotating the roller on a path along said longitudinal axis between said active first position wherein said one location is oriented downwardly toward said base and through one complete revolution of the roller to said active second position wherein said one location is again oriented downwardly toward said base.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

Figure 1:
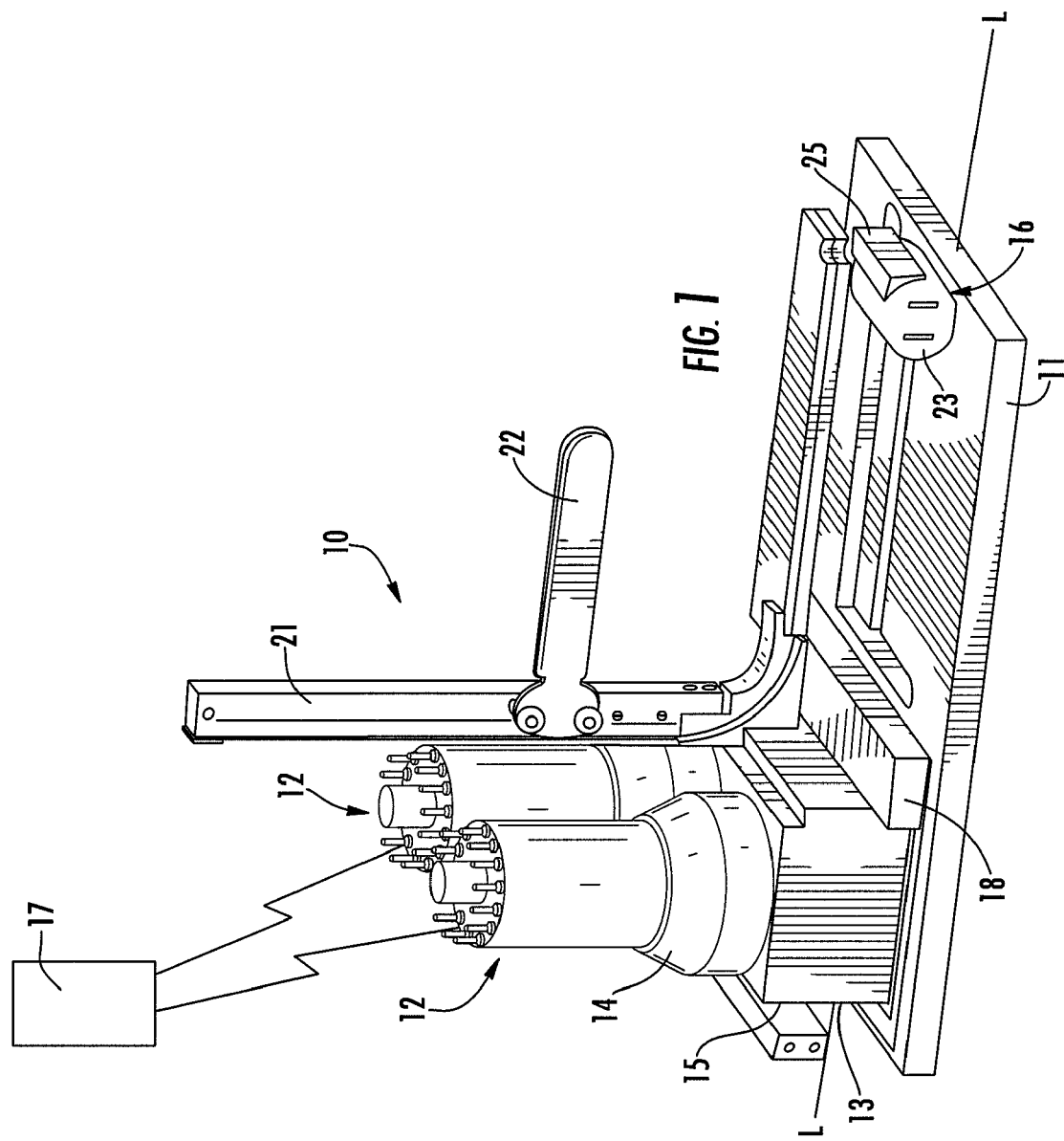
FIG. 1 is a fragmentary perspective rendering showing several of the component parts of a nuclear gauge in accordance with one embodiment of the present invention.

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

The present invention is based on the scattering and absorption properties of gamma radiation with matter. For gamma radiation with energies less than 2 MeV, there are two dominant interacting mechanisms with matter. In the 0.1 to 2 MeV energy range, the dominant mechanism is inelastic scattering (Compton scattering). For energies less than 0.1 MeV, the dominant mechanism is photoelectric absorption. In the 0.1 to 2 MeV energy range, the amount of gamma radiation scattering (energy degradation) is a function of electron density of the material and therefore, density is a fundamental measurement property. This results in a nuclear attenuation per unit-length mass-density that is less influenced by the material composition. At energies below 0.1 MeV, the photoelectric absorption of gamma radiation is sensitive to the atomic number of the material and hence to the chemical (elemental) composition of the material. Therefore, when a gamma radiation source of sufficient energy is placed near a material, and an energy selective gamma radiation detector is used for gamma radiation detection, gamma radiation mainly undergoing Compton scattering can be counted exclusively. With proper calibration, the gamma radiation count can be converted to an absolute density.

According to one specific embodiment of the invention, a $^{137}$Cs gamma radiation source with a 0.662 MeV primary energy is used. However, other gamma radiation sources with different primary energy levels could be employed, such as $^{60}$Co for example. Gamma radiation interacting with the sample is measured with a detector, which is preferably an energy selective detector configured to detect gamma radiation in a predetermined energy spectrum. Gamma radiation detectors may be configured in various ways to be selective to a desired energy spectrum. For example, in the embodiment shown and described herein, an energy selective scintillation detector is used, specifically a sodium iodide (NaI) crystal mounted on a photomultiplier tube (PMT). When using a $^{137}$Cs source, gamma radiation interacting with the sample with energies in the predetermined range 0.1 to 0.4 MeV is counted. In a further specific embodiment, gamma radiation with energies in the predetermined range of 0.1 to 0.25 MeV is counted. The gamma radiation within this energy spectrum is that which has interacted with the underlying material and has been backscattered to the detector. Because of Compton scattering, the radiation posses a lower energy level than the 0.662 MeV primary energy of the $^{137}$Cs source. For gamma radiation sources other than $^{137}$Cs, the upper limit would be selected in a similar manner based upon the energy distribution for the particular source selected.

FIG. 1 is a perspective view illustrating the principal components of a nuclear gauge in accordance with one embodiment of the present invention. For clarity of illustration, some components have been omitted. As shown in FIG. 1, the gauge, generally indicated at 10, includes a base 11 in the form of a rigid gamma radiation transmissive material such as aluminum or a composite material. The base has a flat lower surface adapted to be positioned on a sample of material. As shown, the base is of a generally rectangular configuration and has a longitudinal axis L extending parallel to the length dimension and a transverse or width dimension somewhat smaller than the length dimension. Two gamma radiation detector assemblies, indicated at 12, are mounted at one end of the base 11 in side-by-side relation to one another. The gamma radiation detectors 12, more particularly, are scintillation detectors that generate electrical signals proportional to the energy of gamma rays received by the detector. In the illustrated embodiment, each gamma radiation detector assembly 12 includes a sodium iodide (NaI) crystal 13 mounted to the base 11 and a photomultiplier tube 14 (PMT) mounted above the sodium iodide crystal 13. Each detector assembly may also include an optical filter 15, such as a block of quartz, located between the sodium iodide crystal 13 and photomultiplier tube providing an optical path between the sodium iodide crystal 13 and the photomultiplier tube 14. When gamma radiation strikes the sodium iodide crystal, photons are emitted, which in turn, are detected by the photomultiplier tube and converted into electrical signals. In the embodiment illustrated, the sodium iodide crystals 13 have a square shape and are mounted in side-by-side relation on opposite sides of a central longitudinal axis extending parallel to the length dimension of the base 11. This arrangement augments the effective detector area for receiving backscattered gamma radiation and thus provides increased sensitivity for detecting gamma radiation that is backscattered from the underlying material sample.

At the opposite end of the base 11 from the gamma radiation detectors 12 there is a gamma radiation source mounted in a source mount assembly 16. Gamma radiation from the source emanates downwardly through the base 11 and into an underlying material sample. The gamma radiation interacts with the material of the sample and is backscattered backed up to the detector assemblies 12. The signals from the gamma radiation detector assemblies 12 are processed by a signal processing module 17 and a value for the density of the underlying material sample is determined.

As shown in FIG. 1, a block of radiation shielding material 18 is mounted alongside the sodium iodide crystals 13 of the detector assemblies to prevent gamma radiation originating at the source from passing parallel to the base and directly into the sodium iodide crystal. Thus, only radiation that passes directly into the underlying material sample and interacts with the material sample will be received by the detectors.

The gauge also includes a handle assembly mounted to the base to allow for lifting and moving the gauge. The handle assembly, more particularly, includes a support post 21 extending vertically upwardly from the base 11 and an actuator handle 22 extending laterally from the support post 21.

The handle can be moved upwardly and downwardly along the support post 21 as explained more fully below.

Figure 2:
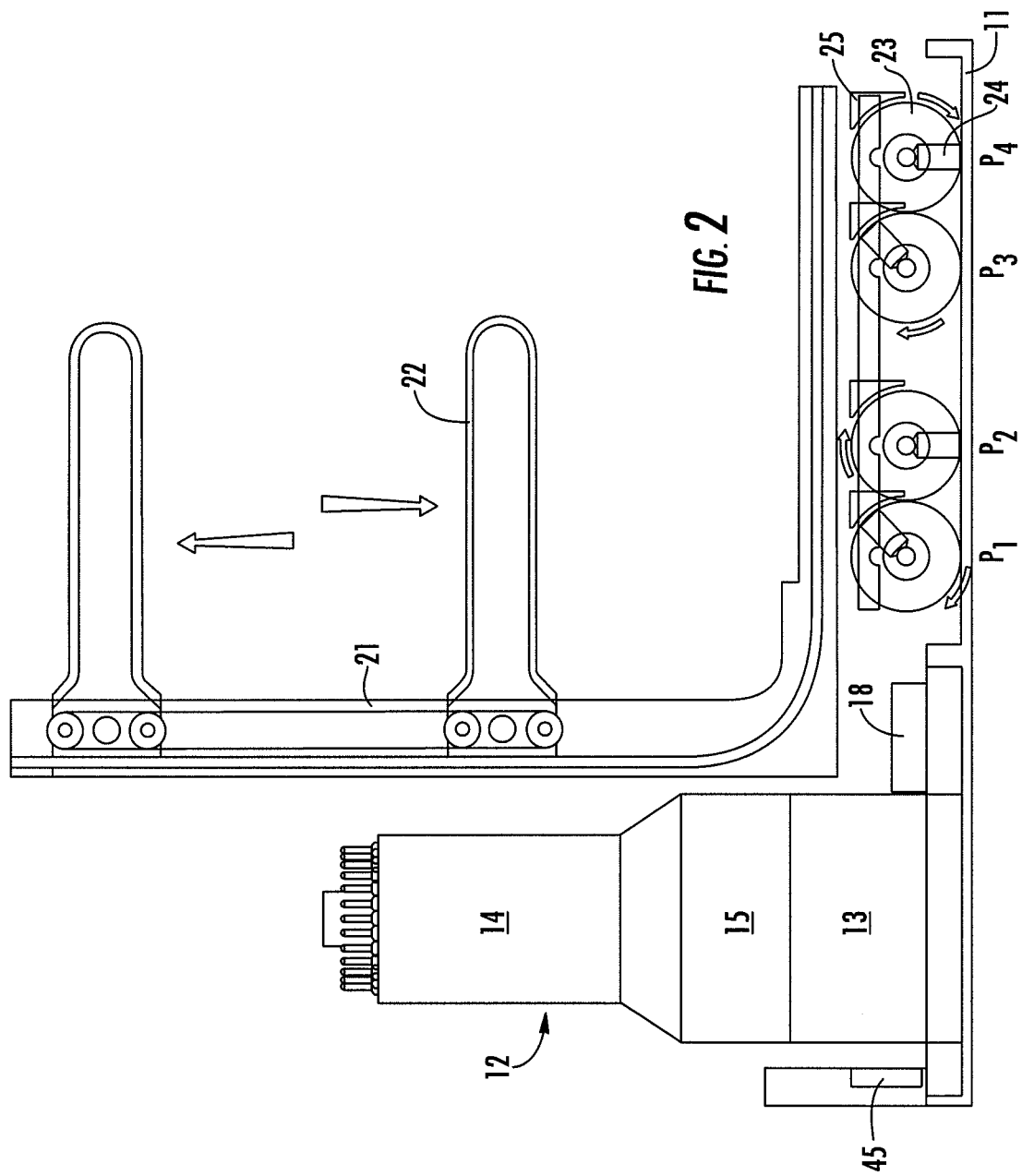
FIG. 2 is a side elevation view of the gauge showing the source mount at several different locations.

Referring to FIG. 2, the source mount assembly 16 includes a cylindrical roller, indicated by the reference character 23, formed of a radiation shielding material such as lead and having a cylindrical outer surface. A radially extending bore is formed in the cylindrical roller and a source capsule 24 is mounted in this bore. Thus, gamma radiation from the source 24 emanates from the cylindrical roller 23 at the location of the radial bore. The source capsule 24 contains a gamma radiation source such as for example cesium 137. Preferably, the source has a total activity of no more than 1000 microcuries (micro Ci), more preferably 500 micro Ci or less, and most desirably 300 micro Ci or less.

The cylindrical roller 23 is mounted for rotational movement along a longitudinal axis extending parallel to the length direction of the base 11. A shield 25 in the form of a block of shielding material, such as lead, is mounted adjacent to the cylindrical roller 23 alongside an upper surface thereof. The shield 25 has a curved surface corresponding to the cylindrical curvature of the roller 23.

FIG. 2 depicts the roller 23 at several different locations along its longitudinal path of movement. In the position shown at the left most location and indicated as $P_1$, the source capsule 24 is oriented angularly upwardly and is positioned opposite the shield 25. This is the inactive storage position for the source. As the roller is rotated clockwise, it arrives at a first active position $P_2$ where the source capsule is oriented downwardly toward the base 11 so that gamma radiation can be emitted through the base and into the underlying material sample. As the roller is rotated further clockwise, it arrives at an intermediate position indicated at $P_3$ where the source capsule 24 is again shielded by the shield 25. As the roller is rotated clockwise one full revolution from position $P_2$, it arrives at a second active position $P_4$ where the source 24 is again oriented downwardly for emitting gamma radiation through the base 11 and into the underlying material sample. By this arrangement, the source mount assembly is capable of creating two distinctly different source-to-detector geometries wherein the gamma radiation travels two distinctly different paths through the underlying material sample in reaching the detector assemblies 12.

Movement of the roller 23 from the inactive storage position $P_1$ to the respective active positions $P_2$ and $P_4$ is achieved by moving the actuator handle 22 up and down. In its uppermost position, the handle causes the source capsule to be located in the inactive storage position $P_1$. This insures that when the gauge is lifted by the handle 22, the source will be returned to the inactive storage position $P_1$. As the handle is pushed downwardly, the roller is released from the initial storage position $P_1$ and arrives at a click-stop or detent position corresponding to the active first position $P_2$. As the handle is pushed further downwardly, it dislodges from the first detent position and arrives at a second detent position $P_3$ where the source is again shielded by the shield 25. Movement of the handle further down to the bottommost position causes the roller 23 to be positioned at the second active position $P_4$.

Figure 3:
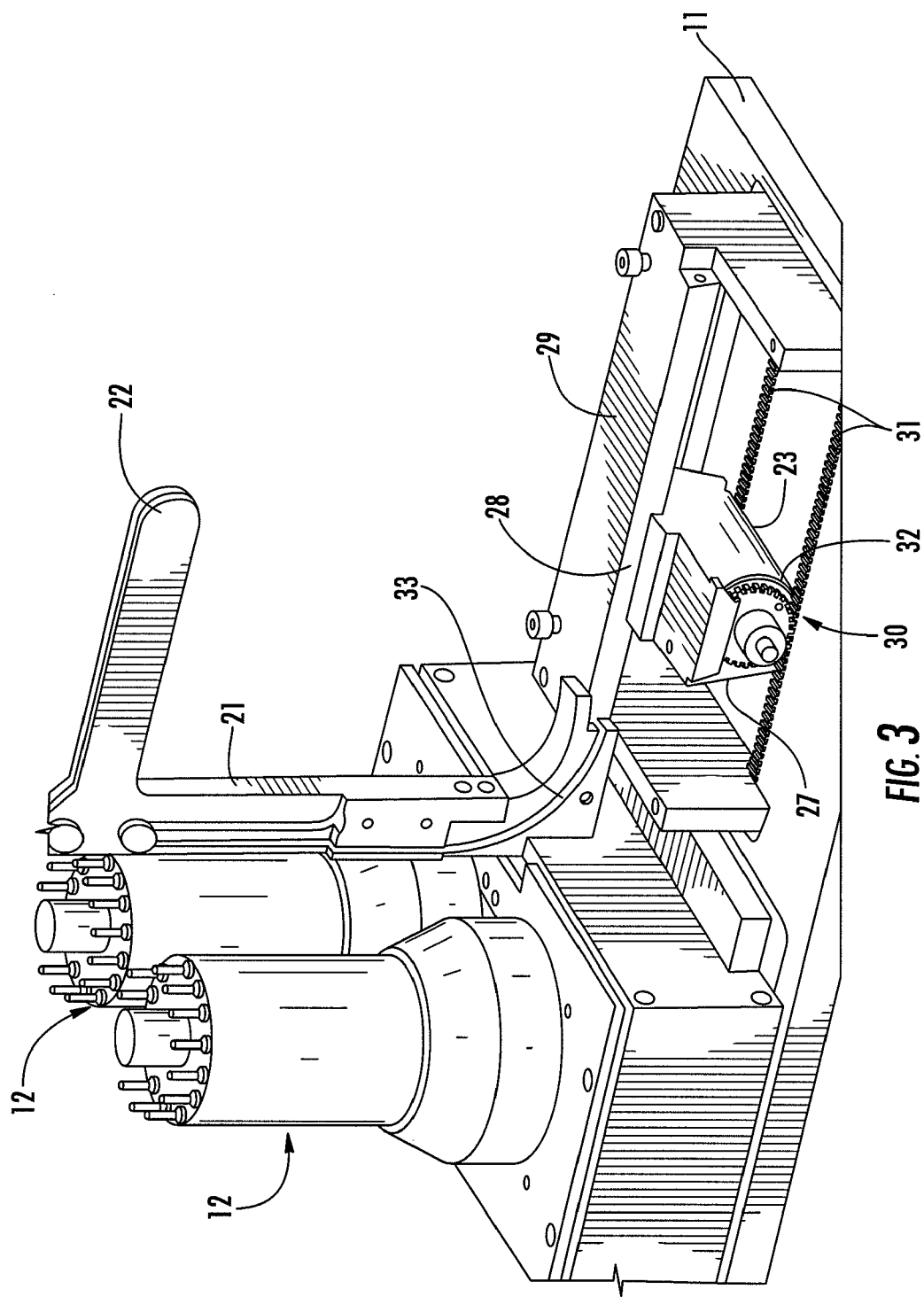
FIG. 3 is an enlarged fragmentary perspective rendering of the gauge.
Figure 4:
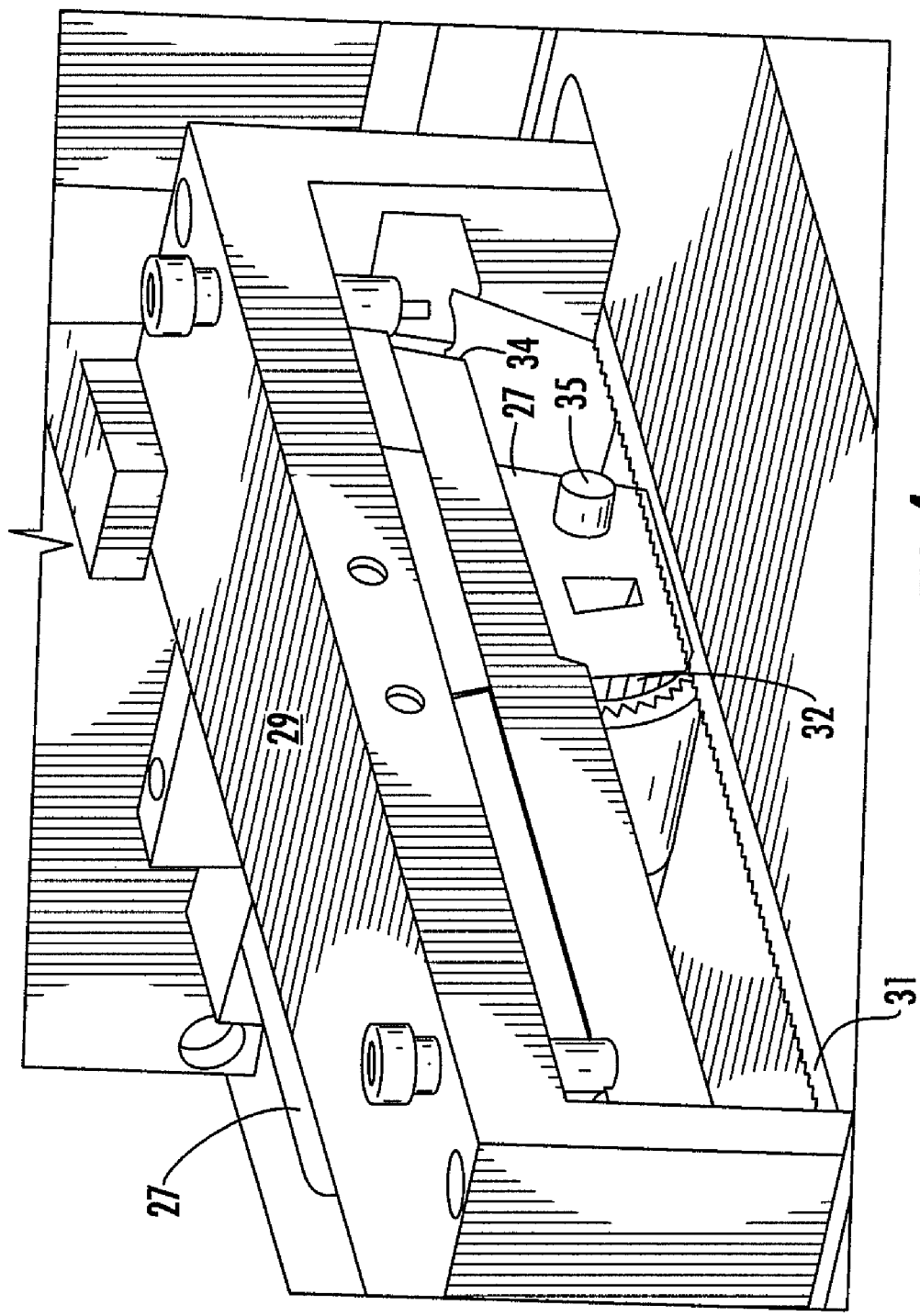
FIG. 4 is an enlarged fragmentary perspective rendering showing details of the source mount.
Figure 5:
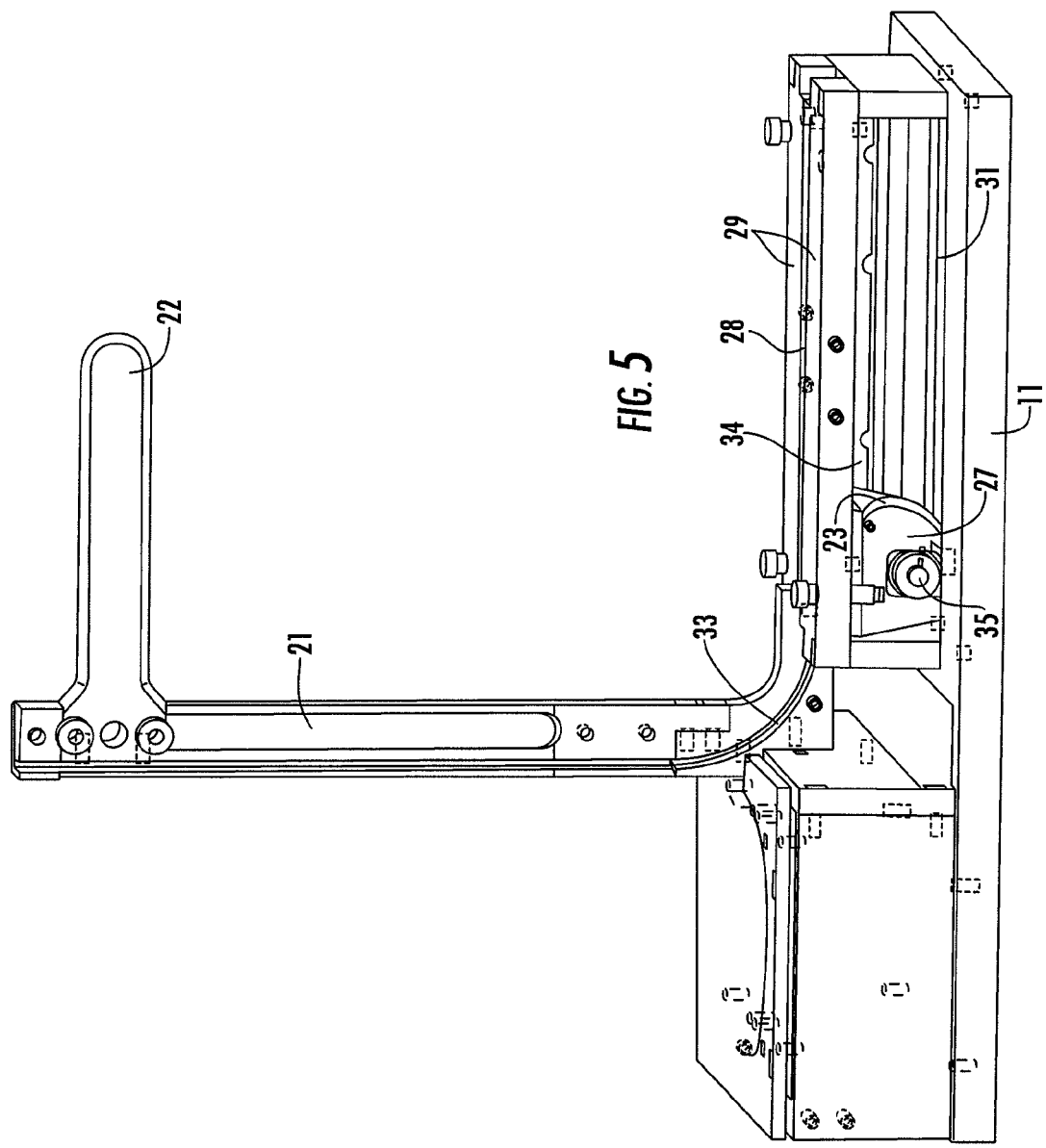
FIG. 5 is a side perspective view showing portions of the gauge.

As best seen in FIG. 3, the roller 23 is mounted for rotating movement in a carriage 27 which is mounted for sliding movement along the longitudinal axis in a trackway 28 defined between a pair of overhead supports 29, only one of which is shown in FIG. 3. To assure consistent and reproducible positioning of the roller at the respective active positions $P_2$ and $P_4$, a rack and pinion assembly 30 cooperates with the roller 23. More particularly, as seen in FIGS. 3 and 4, longitudinally extending rack gears 31 are mounted to the upper surface of the base 11 and cooperating pinion gears 32 are mounted at each end of the cylindrical roller 23, with the teeth of the pinion gears engaging the corresponding teeth of the rack gears 31. A flexible actuator cable 33 is mounted at its upper end to the handle 22 and at its lower end to the carriage 27. Thus, by pushing the handle 22 downwardly, the actuator cable 33 causes the carriage 27 to move longitudinally along the trackway 28. Driven by the rack and pinion assembly 30, the roller 23 rotates at the carriage moves longitudinally along the trackway 28. As best seen in FIGS. 2 and 4, a notched bar 34 is mounted adjacent one side of the roller carriage 27 and is adapted to engage a shaft or axle 35 extending from one end of the roller 23. The notched bar 34 is biased against the surface of axle 35 and the surface of the notched bar is configured to provide inner and outer limits to the path of travel of the roller 23 corresponding to positions $P_1$ and $P_4$, as well as two intermediate detent positions corresponding to positions $P_2$ and $P_3$.

Figure 6:
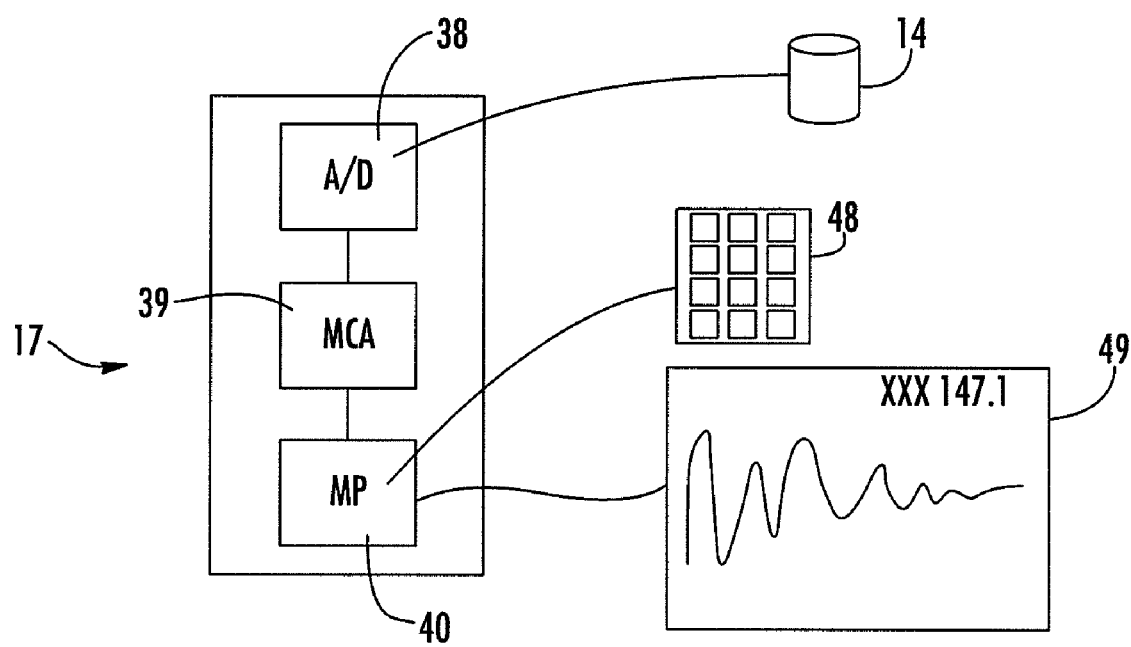
FIG. 6 is a schematic diagram illustrating components of the module used for processing signals from the gamma radiation detector.

The functional components of the signal processing module 17 are shown schematically in FIG. 6. An analog-to-digital converter 38 transforms amplified analog signals from the photomultiplier tubes 14 into digital signals quantifying the energy level of the gamma radiation (photon) count. The output of the analog-to-digital converter 38 is directed to an analyzer device, which in the illustrated embodiment is a multi-channel analyzer (MCA) 39 which accumulates the number of gamma radiation (photon) counts of different energy levels into a plurality of channels, each channel corresponding to portion of the energy level spectrum. For purposes of density calculation, only a predetermined portion of the overall energy spectrum detected by the detectors is considered. Thus, only the accumulated counts from one or more of the channels corresponding to this predetermined portion are considered for the density calculation. For example, in one specific embodiment, this energy spectrum has a lower limit of 0.1 MeV and an upper limit of 0.4 MeV when a $^{137}$Cs gamma radiation source is used. In a more specific embodiment, the lower limit is 0.1 MeV and the upper limit is 0.25 MeV. Other channels of the analyzer representing other slices of the energy spectrum may be considered for taking standard counts or in compensating for background radiation. The output of the MCA 39 is directed to a processor 40 containing a set of stored instructions suitable for converting the accumulated gamma radiation (photon) counts from the MCA into a density value. The processor 40 is operatively connected to a keypad input device 48 and to a suitable output display 49.

Scintillation detectors are sensitive to temperature fluctuations. In the digital spectrum produced by the MCA, the energy level of the gamma radiation detected by the scintillation detector is correlated into one of many (e.g. 512) channels representing the counts corresponding to a particular gamma radiation energy level or range. This spectrum may be represented graphically as extending in the x-direction, with the total number of counts in each channel extending in the y-direction. When the temperature fluctuates, the spectrum fluctuates non-linearly in the x-direction. Therefore, a peak once centered on one channel may end up centered on a different channel. If one wants to find the gamma radiation (photon) counts in channels between $C_{lower}$, representing the energy $E_{lower}$, and $C_{upper}$, representing the energy $E_{upper}$, because of these fluctuations, the counts obtained from using the "raw" spectrum will have uncertainties due to the temperature sensitivity. An analog or digital spectrum stabilizer is used to stabilize the spectral drifts resulting from temperature fluctuations in the NaI detector. For purposes of spectrum stabilization, the gauge is provided with an additional 1 microcurie $^{137}$Cs gamma radiation reference source 45 mounted near the detector 22 in the embodiment shown in FIG. 2. The 0.056 MeV peak from the source 45 is used as a reference point by the MCA for stabilization of the spectrum.

The calculation of the density of a material sample is preferably carried out by a suitably programmed microprocessor or by any other functionally equivalent device, such as an application specific integrated circuit or a general purpose computer. The gauge is placed on the sample to be measured and a count is obtained for a suitable period of time. From the MCA, stabilized counts for the particular portion of the energy spectrum of interest are obtained. The procedures for calibrating the gauge and for calculating density are described more fully in commonly owned U.S. Pat. No. 6,567,498, the contents of which are incorporated herein by reference. In a preferred implementation, the calculations for density are carried out on the accumulated gamma radiation (photon) counts repeatedly at frequent intervals as the counting proceeds, such as every one to two seconds, treating each as a frequency packet, and a digital filtering algorithm is utilized to decrease the statistical variation of the packet. This approach makes it possible to provide to the user an almost real-time display of the calculated density value while the count is still proceeding.

Figure 7:
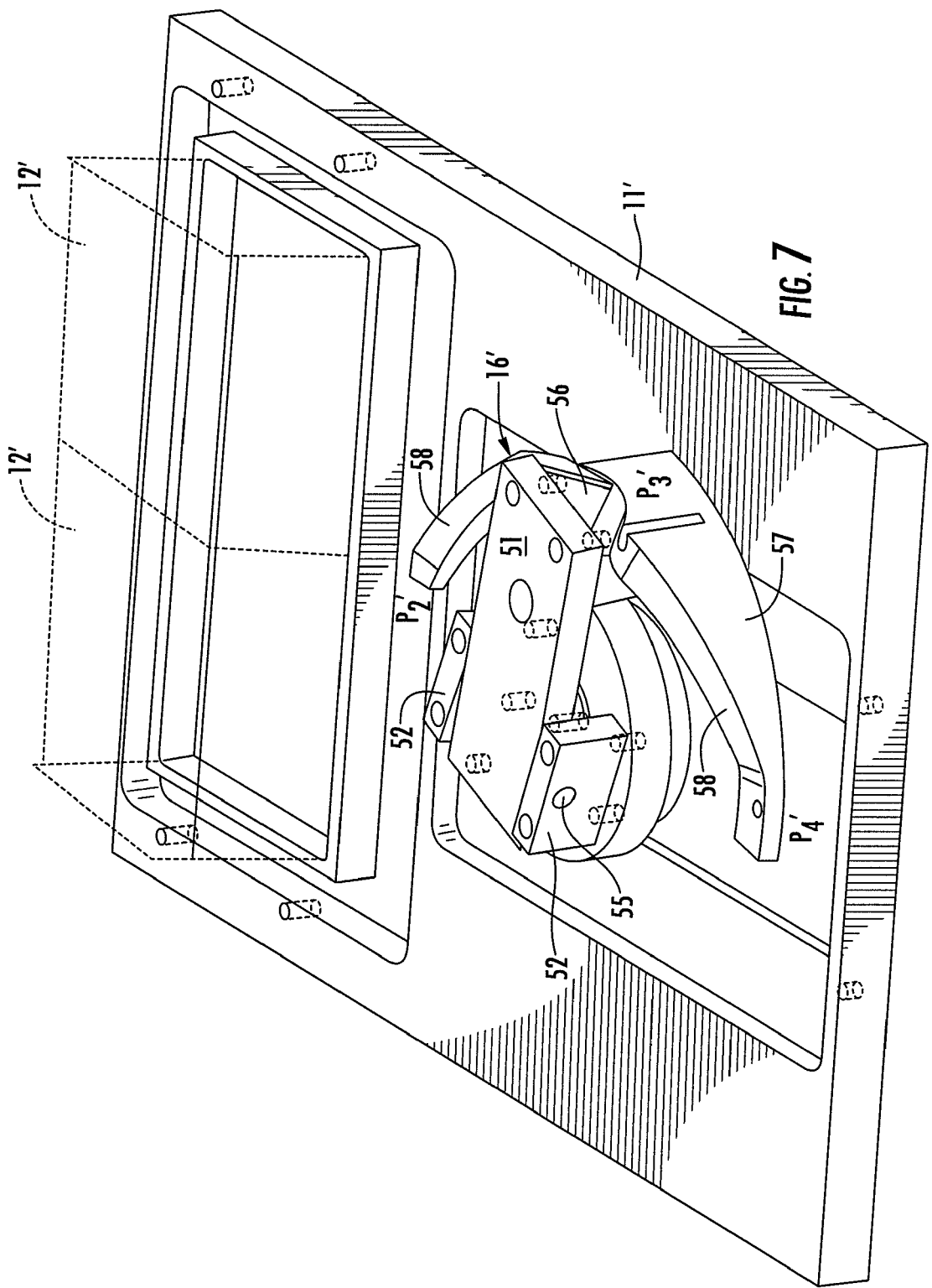
FIG. 7 is a perspective view showing another embodiment of a source mount in accordance with the present invention.

FIG. 7 illustrates an alternative embodiment for the source mount. To avoid repetitive description, elements in this embodiment that correspond to elements previously described will bear the same reference numbers, with prime (') notation added. This embodiment differs over the previous embodiment primarily in that the source mount assembly 16' moves the source along a non-linear path from the active first position to the active second position, rather than along a linear path corresponding with the longitudinal axis of the base. As illustrated, the source mount assembly 16' includes an arm 51 that is pivotally mounted at one end and carries the source at its opposite end. By rotating the arm about its pivotal mounting point, the source is moved along an arcuate path between the active first position $P_1'$ close to the detector and the active second position $P_4'$ further away from the detector along the longitudinal axis of the base 11'. More particularly, the arm 51 is attached to mounting blocks 52 which, in turn, are mounted to the upper surface of a turntable 53. The turntable 53 is mounted to the base 11' for pivotal movement about a central axis. The arm 51 is connected to the mounting blocks 52 by a pivot pin 55 which thus allows for the opposite end of the arm 51 to pivot upwardly. The source capsule is mounted in an enclosure 56 that projects downwardly from the lower surface of the arm 51. An articulately shaped ramp 57 is mounted to the base 11' and lies along an arcuate path traced by the enclosure 56 when the arm 51 is rotated. The ramp 57 is formed of a gamma radiation shielding material, such as lead, and is configured with an upper surface 58 that tapers upwardly from an first active position $P_2'$ located closest to the detectors 12, reaching its highest point at a location indicated at $P_3'$ about a 90 degree rotation from position $P_2'$ and then tapering back downwardly during the next 90 degrees of rotation, where the arm reaches the active second position $P_4'$. At the highest point $P_3'$, a cavity is formed in the ramp 57 configured for receiving the enclosure 56 therein. By this arrangement, as the arm 51 is rotated through 180°, the enclosure rides along the upper surface 58 of the ramp as it moves from the active first position $P_2'$ to an intermediate inactive position $P_3'$ where the enclosure 56 is received within the cavity and thus shielded by the shielding material of ramp 57. Further rotation of the arm 51 causes the enclosure 56 to ride upwardly out of the cavity and to continue along its arcuate path of travel to the second active position $P_4'$.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A nuclear density gauge comprising
    a base having a surface adapted to be positioned on a surface of a material sample;
    at least one gamma radiation detector carried by said base and mounted at a predetermined location relative to an axis extending longitudinally of the base;
    a gamma radiation source; and
    a source mount carried by the base and mounting the gamma radiation source for movement along a path between an active first position located at a first longitudinal distance from said at least one detector and an active second position located at a second longitudinal distance from said detector, the active first and second positions being substantially equidistant from the surface of the base,
    wherein said at least one gamma radiation detector is positioned and arranged to detect gamma radiation emanating from said source and backscattered from the underlying material sample through a first path of travel when the source mount is at said first active position and through a second path of travel when the source mount is at said second active position.

2. The gauge of claim 1, wherein said source mount includes means for moving the source from said active first and second positions to an inactive third position shielded by gamma radiation shielding material.

3. The gauge of claim 1, wherein said source mount is constructed and arranged to move the source linearly along a longitudinal path between said first and second active positions.

4. The gauge of claim 3, wherein said source mount includes a roller formed of a gamma radiation shielding material and having a cylindrical outer surface, and wherein said source is mounted in the roller so that the gamma radiation from the source emanates from one location on the cylindrical surface, and including means for rotating the roller on a path along said longitudinal axis between said active first position wherein said one location is oriented downwardly toward said base and through at least one complete revolution of the roller to said active second position wherein said one location is again oriented downwardly toward said base.

5. The gauge of claim 4, wherein said means for rotating the roller comprises an elongate rack gear extending parallel to said longitudinal axis and a cooperating pinion gear associated with the roller.

6. The gauge of claim 5, including an external actuator operable for allowing an operator of the gauge to move the roller between said first and second active positions.

7. The gauge of claim 6, including gamma radiation shielding material positioned adjacent the cylindrical surface of said roller and oriented for overlying said one location on the cylindrical surface when the roller is rotated to an inactive third position to thereby shield the gamma radiation source.

8. The gauge of claim 7, including a handle mounted to the base to permit manually lifting the gauge, and wherein said actuator is associated with the handle and operable for moving the roller to said inactive third position when the gauge is lifted by the handle.

9. The gauge of claim 1, wherein said source mount is constructed and arranged to move the source along a non-linear path between said first and second active positions.

10. The gauge of claim 9, wherein the source mount includes an arm that is pivotally mounted at one end and carries the source at its opposite end, and including means for rotating the arm about its pivotal mounting point so that the source is moved along an arcuate path between the active first position closer to the detector and the active second position further away from the detector.

11. The gauge of claim 1, wherein said at least one gamma radiation detector comprises first and second gamma radiation detectors carried by said base and mounted in side-by-side relationship on opposite sides of an axis extending longitudinally of the base.

12. The gauge of claim 1, wherein said gamma radiation source has total activity of no more than 500 microcuries, and said at least one gamma radiation detector comprises a scintillation detector.

13. A nuclear density gauge comprising
a base having a surface adapted to be positioned on a surface of a material sample;
first and second gamma radiation detectors carried by said base and mounted at a predetermined location relative to an axis extending longitudinally of the base;
a gamma radiation source having a characteristic primary energy and a total activity of no more than 500 microcuries;
a source mount carried by the base and mounting the gamma radiation source for longitudinal movement along said axis between an active first position located at a first longitudinal distance from said first and second detectors and an active second position located at a second longitudinal distance from said detectors, the active first and second positions being substantially equidistant from the surface of the base; and
means for calculating a value for the density of the material sample based upon the gamma radiation detected by said first and second detectors.

14. The gauge of claim 13, wherein said first and second gamma radiation detectors are mounted in side-by-side relationship on opposite sides of said axis.

15. The gauge of claim 13, wherein said source mount includes means for moving the source from said active first and second positions to an inactive third position shielded by gamma radiation shielding material.

16. The gauge of claim 13, wherein said source mount includes a roller formed of a gamma radiation shielding material and having a cylindrical outer surface, and wherein said source is mounted in the roller so that the gamma radiation from the source emanates from one location on the cylindrical surface, and including means for rotating the roller on a path along said longitudinal axis between said active first position wherein said one location is oriented downwardly toward said base and through one complete revolution of the roller to said active second position wherein said one location is again oriented downwardly toward said base.

17. The gauge of claim 16, wherein said means for rotating the roller comprises an elongate rack gear extending parallel to said longitudinal axis and a cooperating pinion gear associated with the roller.

18. The gauge of claim 17, including an external actuator operable for allowing an operator of the gauge to move the roller between said first and second active positions.

19. The gauge of claim 18, including gamma radiation shielding material cooperating with said roller and positioned opposite said one location on the roller when the roller is moved to said inactive third position.

20. The gauge of claim 19, including a handle mounted to the base to permit manually lifting the gauge, and wherein said actuator is associated with the handle and operable for moving the roller to said inactive third position when the gauge is lifted by the handle.

21. A nuclear density gauge comprising
a base having a surface adapted to be positioned on a surface of a material sample;
first and second gamma radiation scintillation detectors carried by said base and mounted in side-by-side relationship on opposite sides of an axis extending longitudinally of the base, detectors each including a photon-emitting crystal and a photomultiplier tube cooperating with the photon-emitting crystal for generating electrical signals proportional to the intensity of the photons, and wherein said crystals are of a square shape and are positioned next to one another on opposite sides of said longitudinal axis to form a rectangle with a longer dimension extending transverse to the longitudinal axis;
a gamma radiation source having a characteristic primary energy and a total activity of no more than 500 microcuries;
a source mount carried by the base and movably mounting the gamma radiation source at a location spaced along said longitudinal axis from said first and second detectors; and
means for calculating a value for the density of the material sample based upon the gamma radiation detected by said first and second detectors.

22. The gauge of claim 21, wherein said source mount includes a roller formed of a gamma radiation shielding material and having a cylindrical outer surface, and wherein said source is mounted in the roller so that the gamma radiation from the source emanates from one location on the cylindrical surface, and including means for rotating the roller on a path along said longitudinal axis between said active first position wherein said one location is oriented downwardly toward said base and through one complete revolution of the roller to said active second position wherein said one location is again oriented downwardly toward said base.

23. The gauge of claim 21, wherein said source comprises $^{137}$Cs having a total activity of no more than 300 microcurie.

* * * * *

UNITED STATES PATENT AND TRADEMARK OFFICE
CERTIFICATE OF CORRECTION

| | |
|---|---|
| PATENT NO. | : 7,605,366 B2 |
| APPLICATION NO. | : 11/534075 |
| DATED | : October 20, 2009 |
| INVENTOR(S) | : Dep et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 216 days.

Signed and Sealed this

Fifth Day of October, 2010

David J. Kappos
*Director of the United States Patent and Trademark Office*